United States Patent
Besson

(10) Patent No.: US 6,339,632 B1
(45) Date of Patent: Jan. 15, 2002

(54) MULTI SLICE SINGLE FILTERING HELICAL WEIGHTING METHOD AND APPARATUS TO USE THE SAME

(75) Inventor: Guy M. Besson, Wauwatosa, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/470,770

(22) Filed: Dec. 23, 1999

(51) Int. Cl.[7] .................................................. H61B 6/03
(52) U.S. Cl. ........................................ 378/15; 378/901
(58) Field of Search .............................. 378/4, 15, 901

(56) References Cited

U.S. PATENT DOCUMENTS

| 5,469,486 A | 11/1995 | Hu et al. ........................ 378/4 |
| 5,960,056 A | * 9/1999 | Lai ................................ 378/4 |
| 6,002,738 A | * 12/1999 | Cabral et al. ................... 378/4 |
| 6,118,841 A | * 9/2000 | Lai ............................... 378/19 |

OTHER PUBLICATIONS

*Multi–sclice Helical CT: Scan and Reconstruction*, Med. Phys. 26 (1), Jan. 1999 Am. Assoc. Phys. Med, pp 1–14, Hui Hu.
*CT Image Reconstruction from Fan–Parallel Data*, Med. Phys. 26 (3), Aug. 1999 Am. Assoc. Phys. Med, pp 415–426.
*New Classes of Helical Weighting Algorithms with Applications to Fast CT Reconstruction*, Med. Phys. 25 (8), Aug. 1998 Am. Assoc. Phys. Med, pp 1521–1532, Guy Besson.

* cited by examiner

Primary Examiner—David V. Bruce
(74) Attorney, Agent, or Firm—Quarles & Brady, LLP; Christian G. Cabou

(57) ABSTRACT

A method for rapidly processing multi-slice helical fan beam CT imaging data to generate tomographic images, the method including processing the fan beam helical data to generate parallel constant-Z projections proximate an image plane, filtering the parallel constant-Z projections and mathematically combining the filtered parallel constant-Z projections as a function of the spatial relationship between the imaging plane and the constant-Z projections to generate at least one image.

8 Claims, 5 Drawing Sheets

FIG. 1
PRIOR ART
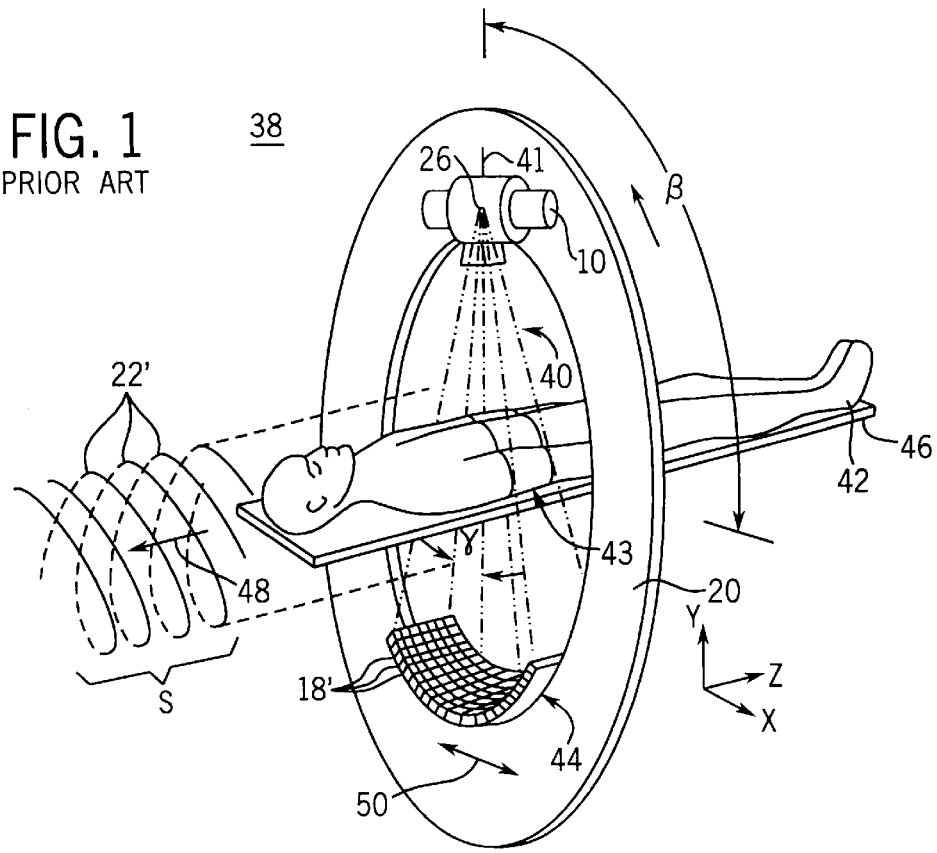
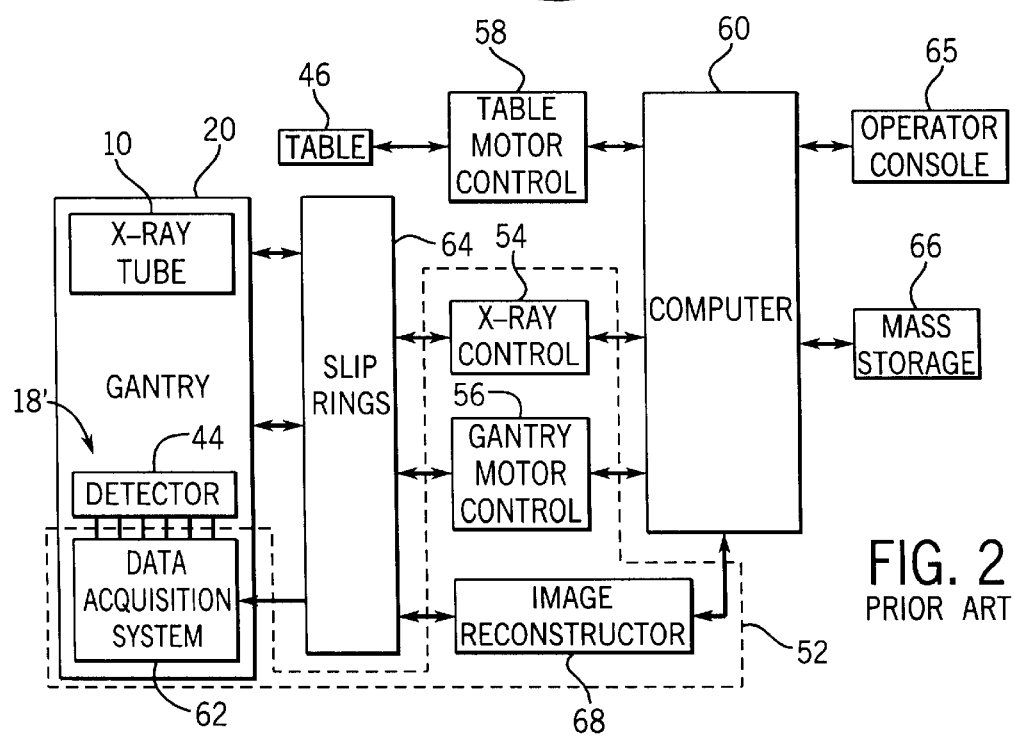
FIG. 2
PRIOR ART

MULTI SLICE SINGLE FILTERING HELICAL WEIGHTING METHOD AND APPARATUS TO USE THE SAME

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to multislice helical computerized tomography and more particularly to an algorithm, method and apparatus for using the same which reduces the data processing time required to generate an image.

In computerized tomography (CT) x-ray photon rays are directed through a patient toward a detector array. Attenuated rays are detected by the array, the amount of attenuation indicative of the make up (e.g. bone, flesh, air pocket, etc.) of the patient through which the rays traversed. The attenuation data is then backprojected to generate an image of the patient's internal anatomy.

Early CT systems used a pencil beam photon source consisting essentially of a single ray and a single detector. To collect a complete projection from a single angle about the patient the pencil beam was directed at the patient consecutively from adjacent locations along a line thereby generating parallel ray data for the projection. Other parallel ray projections through the same patient slice from different angles about the slice were generated in the same manner. After multiple (e.g., 500 or more) parallel projection data sets were generated for a slice, the data was backprojected to form a slice image. Because early CT systems generated parallel projection data sets, most CT reconstruction algorithms have been developed assuming parallel data sets.

Unfortunately, while pencil beam systems generate data in a form readily useful with conventional reconstruction algorithms, such systems have a number of shortcomings. One primary shortcoming is that data acquisition periods using such a system are excessive. This is particularly true where images in many slice planes are required. Not only do long acquisition periods reduce system throughput but long periods also often result in relatively poor images. This is because patient movement likelihood increases as the time required for data acquisition increases and patient movement results in blurred images and undesirable artifacts.

Various CT system features and procedures have been developed to increase data acquisition speed including fan beam acquisition, simultaneous multiple slice acquisition and helical scanning. In fan beam systems, instead of using a pencil beam source, the source is collimated into a thin fan beam which is directed at a detector array on a side opposite a patient. In this manner, a complete fan beam projection data set is instantaneously generated for the angle defined by the source during a single data acquisition period and data collection is expedited.

In multiple slice systems, a relatively thick fan beam is collimated and directed at a multi-row detector with a patient therebetween, each detector row in effect gathering data for a separate slice of the thick fan beam along a Z axis perpendicular to the direction of the fan beam.

In a helical scanning system, the source and detector array are mounted on opposing surfaces of an annular gantry and are rotated therearound as a patient is transported at constant speed through the gantry, the x-ray beam sweeps a helical path through the patient, hence the nomenclature "helical scanning system". Data acquisition can be sped up by increasing the pitch or table translation speed/gantry rotation ratio. Increased pitch typically results in less detailed imaging.

Various combinations of the fan-beam, multislice and helical scanning features have been combined to realize synergies and have been somewhat successful. By combining all three speed enhancing features data acquisition periods are appreciably reduced thereby increasing system throughput and increasing image quality by minimizing the likelihood of patient movement.

While the features described above speed up data acquisition, the resulting data is not in a form which is readily useable with the conventional image reconstruction algorithms. Whereas the conventional algorithms require parallel constant-Z data for reconstruction, data generated using the optimal fast hardware configuration and generation methods generate fan beam (i.e., non-parallel) data for many projections which are not in the same slice (i.e. are multi-Z). Thus, for example, data for two projections will include two separate fan beam projection data sets, a first set at one Z-location and a second set at another Z-location where Z is the axis of gantry rotation.

Not surprisingly, because of data acquisition speed advantages, various algorithms and methods have been developed to generate constant-Z slice images from helical multi-slice fan beam data. To this end, exemplary algorithms require a processor to solve complex and computationally detailed weighting and filtering equations to generate data suitable for backprojection algorithms. Exemplary weighting algorithms are described in an article entitled "*Multi-Slice Helical CT: Scan and Reconstruction*" by Hui Hu which was published in the January 1999 issue of Medical Physics, vol. 26, No. 1, pages 1 through 14. In operation, after imaging data has been collected and archived for a specific patient volume (i.e. 3 dimensional section) of interest, an imaging system operator can select a specific slice and slice thickness through the volume of interest for image reconstruction and display. When a slice is selected, the processor applies the weighting and filtering function to the data to generate the intended image. The weighting function is dependent upon which slice is selected for reconstruction and viewing. Therefore, each time a new slice is selected, a completely different weighting function which is pitch and slice dependent, has to be accessed and applied to the acquired data and the weighted projection data has to be refiltered again to generate the desired image.

Because the filtering and weighting algorithms are extremely complex, data processing is not fast enough to support instantaneous imaging. Thus, after a slice to be imaged is selected, processing requirements cause a delay. The delay is repeated each time a new slice to be imaged is selected. While this process of selection, weighting, evaluation and reselection may not be objectionable where a system user generally knows the slice or slices which should be examined and therefore may only need to be repeated a few times, in some cases the user will not know which images are important and will therefore have to go on a "fishing" expedition requiring many iterative image reconstruction sequences. Moreover, where three-dimensional imaging or fluoroscopy techniques are employed most systems require reconstruction of two or more (e.g., some times 6, 12, etc) images per source rotation to generate images having diagnostic quality Z-resolution and temporal resolution. In these cases required reconstruction time is excessive.

Other relatively fast acquisition/processing systems/ methods have been developed which include other combinations of fan-beam, multi-slice and helical scanning features. For example, one such system described in an article entitled "New Classes of Helical Weighting Algorythms With Applications to Fast CT Reconstruction" by Guy Besson which was published in Med. Phys. 25(8), August 1998 by Am. Assoc. Phys. Med. combines single slice fan beam data acquisition and helical scanning. As taught in the Besson article such a system is typically used to generate fan beam projections during a single $2\pi$ rotation about a patient. Thereafter, the fan beam data is filtered, weighted and backprojected to generate one or more images in various constant Z planes.

Unfortunately, weighting algorithms used with these single slice systems include a fan beam angle dependency and do not lend themselves to fast image reconstruction. This is because, as known in the art, weight distributions present a line of discontinuity across the space of projections which defines two separate sinogram regions. The weighting function expressions differ for the two separate regions. For this reason, reconstruction of P different image planes using a given projection requires P weightings and filterings of that projection.

The Besson article teaches one data processing approach for use with single slice helical fan beam data which reduces processing time appreciably by requiring only one filtering per projection regardless of the number P of image planes required. To this end, the Besson article teaches that single slice fan beam data can be re-binned into multi-Z parallel projections wherein the rays in each parallel projection have the same projection angle. Thus, filtering of the parallel projections need only be performed once to account for the ray parameter.

After filtering, the filtered multi-Z projection data is used to backproject and generate different images within various image planes. Each image is generated as a function of the distance along the Z-axis between a central ray in each filtered multi-Z projection and the plane corresponding to the particular image. In other words, the distances between the rays in each multi-Z projection and the image plane are estimated as being the distance between the central ray in the projection and the image plane.

Unfortunately, the above described system also has a number of shortcomings. Among others, one important shortcoming is that the assumption made during backprojection and helical weighting to generate a planar image introduces an error into the imaging data. This is because, while the estimate is accurate for the central ray in a multi-Z projection, the estimate is less accurate for rays which are positioned laterally in the projection (i.e., each projection consists of multi-Z rays and hence the distance along Z between projection rays and a constant Z image plane is different for each ray).

Another shortcoming is that data acquisition is relatively slow with this single imaging plane architecture (i.e. a single slice detector) when compared to the multi-slice detectors described above.

BRIEF SUMMARY OF THE INVENTION

An exemplary embodiment of the present invention includes a method for use with a CT system which includes a fan beam source and a multi-row detector arranged on opposite sides of a Z-axis wherein the source and detector are rotated about the Z-axis as a patient traverses therealong to generate helical imaging data, the method for generating at least one image within an imaging plane from the helical data. The method comprises the steps of, after fan beam helical imaging data has been acquired, processing the data to generate parallel constant-Z projections proximate the imaging plane, filtering the parallel constant-Z projections and mathematically combining the parallel constant-Z projections as a function of the spatial relationship between the imaging plane and the constant-Z projections to generate at least one image.

Preferably the processing step includes rebinning the fan beam data into parallel multi-Z projections which include parallel rays at different locations and mathematically combining the parallel multi-Z projections to generate the parallel constant-Z projections.

In one embodiment the step of mathematically combining the multi-Z projections includes the step of interpolating between adjacent projections. In another embodiment the step of mathematically combining multi-Z projections includes the step of extrapolating among projections.

In one aspect the step of mathematically combining as a function of the spatial relationships includes the step of mathematically combining as a function of the distances in Z between the imaging plane and the constant-Z projections.

The method is also for generating a second image within a second imaging plane from the helical data and, to this end, comprises the steps of, after filtering, mathematically combining the parallel constant-Z projections as a function of the distance in Z between the second imaging plane and the constant-Z projections to generate the second image.

In another aspect the step of mathematically combining the parallel constant-Z projections includes weighting a sub-set of the constant-Z projections, combining the subset of weighted projections to generate a set of image projections and back-projecting the image projections to generate the image.

Preferably the step of weighting a sub-set includes selecting constant-Z projection pairs, each pair including a first constant-Z projection on a first side of and adjacent the imaging plane and a second constant-Z projection on a second side of and adjacent the imaging plane and weighting each projection pair ray as a function of the distance in Z between the projection including the ray and the image plane and wherein the step of combining the subsets includes, after the projection rays have been weighted, combining the rays in each projection pair into a single projection to be back-projected.

Also, preferably, the method is for generating a second image within a second imaging plane from the helical data and comprising the steps of, after filtering, selecting constant-Z projection pairs, each pair including a first constant-Z projection on a first side of and adjacent the second imaging plane and a second constant-Z projection on a second side of and adjacent the second imaging plane and weighting each projection pair ray as a function of the distance in Z between the projection including the ray and the second image plane, combining the subset of weighted projections to generate a set of image projections and back-projecting the image projections to generate the image.

The invention further includes an apparatus including a processor which runs a pulse sequencing program to perform the methods described above.

BRIEF DESCRIPTION OF THE SEVERAL VIEWS OF THE DRAWINGS

FIG. 1 is a perspective view of a CT apparatus used to practice the present invention which includes a detector array having rows and columns of detector elements and fan beam source;

FIG. 2 is a block diagram of CT control system which may be used to control the CT apparatus of FIG. 1 and which is useful for the purposes of practicing the present invention;

DETAILED DESCRIPTION OF THE INVENTION

Figure 3:
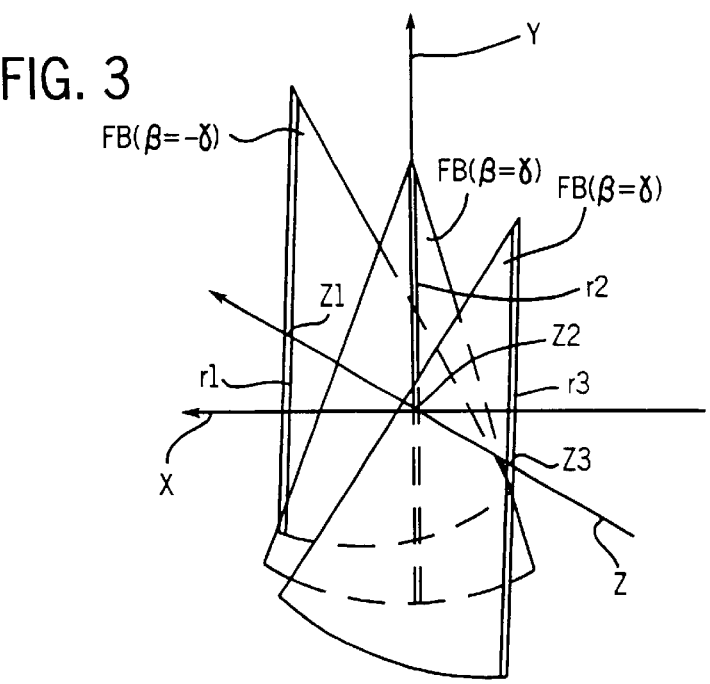
FIG. 3 is a schematic view illustrating three temporally disparate fan beams generated by the fan beam source of FIG. 1.

Referring to FIG. 1, a CT scanner for use with the present invention includes a gantry 20 supporting an x-ray source 10 oriented to project a fan beam 40 of x-rays along the beam axis 41 through a patient 42 to a supported and opposed detector array 44. The gantry 20 rotates to swing the beam axis within a gantry plane 38 defining the x-y plane of a Cartesian coordinate system. Rotation of the gantry 20 is measured by beam angle $\beta$ from an arbitrary reference position within the gantry plane 38.

A patient 42 resets on a table 46 which may be moved along a translation axis 48 aligned with the Z-axis of the Cartesian coordinate system. Table 46 crosses gantry plane 38 and is radiotranslucent so as not to interfere with the imaging process.

The x-rays of the fan beam 40 diverge from the beam axis 41 within the gantry plane 38 across a transverse axis 50 generally orthogonal to both the beam axis 41 and the translation axis 48 at a fan beam angle $\gamma$. The x-rays of beam 40 also diverge slightly from the beam axis 41 and the gantry plane 38 across the translation axis 48. Because this divergence across axis 48 is minimal the divergence is ignored for purposes of this explanation.

After passing through patient 42, the x-rays of the fan beam 40 are received by the detector array 44 which has multiple columns of detector elements 18'. The detector elements 18' are arranged in rows extending along the traverse axis 50 and columns extending along the translation axis 48. The surface of detector array 44 may be planar or may follow a section of a sphere or cylinder having a center at focal spot 26 or on the axis of rotation.

The detector elements 18' each receive x-rays and provide intensity measurements along separate rays of the fan beam 40. Each intensity measurement describes the attenuation via a line integral of one fan beam ray passing through a portion of volume 43 of the patient 42. In a preferred embodiment, volume 43 is greater than the slice volume measured by a conventional single slice fan beam CT system and the width of the detector array 44 is measured along its columns.

Referring now to FIG. 2, the control system of a CT imaging system of FIG. 1 has gantry associated control modules 52 which include an x-ray control 54, a gantry motor control 56, a data acquisition system 62 and an imagery constructor 68. The x-ray control 54 provides power and timing signals to the x-ray source 10 to turn it on and off as required under the control of a computer 60. The gantry motor control 56 controls the rotational speed and position of the gantry 20 and provides information to the computer 60 regarding gantry position. The data acquisition system 62 samples and digitizes intensity signals from the detector elements 18' of detector array 44 and the imagery constructor 68 receives the sampled and digitized intensity signals from the data acquisition system 62 each identified as to column and row of the detector element of the detector array 44, and combines the intensity signals from the detector elements 18' according to the present invention, and performs high speed imagery construction according to methods known in the art.

Each of the above modules is connected to its associated elements on the gantry 20 via slip rings 64 and serves to interface processor or computer 60 to various gantry functions. Slip rings 64 permit the gantry 20 to rotate continuously through angles greater than 360° to acquire projection data.

The speed and position of table 46 along the translation axis 48 is communicated to and controlled by computer 60 by means of table motor control 58. In addition, computer/processor 60 runs a pulse sequencing program to perform the inventive data processing method as described in more detail below. The computer 60 receives commands and scanning parameters via operator console 65 which is generally a CRT display and keyboard which allows an operator to enter parameters for the scan and to display the reconstructed image and other information from the computer 60. A mass storage device 66 provides a means for storing operating programs for the CT imaging system, as well as image data for future reference by the operator. Both the computer 60 and the imagery constructor have associated electronic memory (not shown) for storing data.

In operation, the gantry motor control 56 brings the gantry 20 up to a rotational speed and the table motor control begins translation of the table 46. The x-ray control 54 turns on the x-ray source 10 and projection data are acquired on the continuous basis. At each beam angle $\beta$, the projection acquired comprises intensity signals corresponding to each detector element 18' at each particular column and row of array 44.

A. THEORY

Referring to FIGS. 1 and 3, as gantry 20 is rotated about patient 42 during a data acquisition process, fan beam 40 is directed at patient 42 along different angles $\beta$ thereby acquiring fan beam projection data corresponding to separate fan beams. Three exemplary fan beams are illustrated in FIG. 3 including a first beam $FB(\beta=-\gamma)$, a second beam $FB(\beta=0)$ and a third beam $FB(\beta=\gamma)$, each of beams $FB(\beta=-\gamma)$, $FB(\beta=0)$ and $FB(\beta=\gamma)$ corresponding to a different time during a data acquisition process and where the entire fan beam angle is 2 $\Gamma$. Although not illustrated, data corresponding to many other fan beams directed along different angles between $\beta=-\Gamma$ and $\beta=\Gamma$ is also collected where $\Gamma$ is the maximum ray angle $\gamma$. In addition, data for other angles $\beta$ where angle $\beta$ is greater than $\gamma$ and less than $-\gamma$ (e.g. for 2 $\pi$ or more angles) is also collected. Because patient 42 is translated along axis Z during the acquisition process each fan beam $FB(\beta=-\gamma)$, $FB(\beta=0)$ and $FB(\beta=\gamma)$ is positioned at a relatively different location along the Z-axis. As illustrated, beams $FB(\beta=-\gamma)$, $FB(\beta=0)$ and $FB(\beta=\gamma)$ are at positions Z1, Z2 and Z3, respectively.

Figure 4:
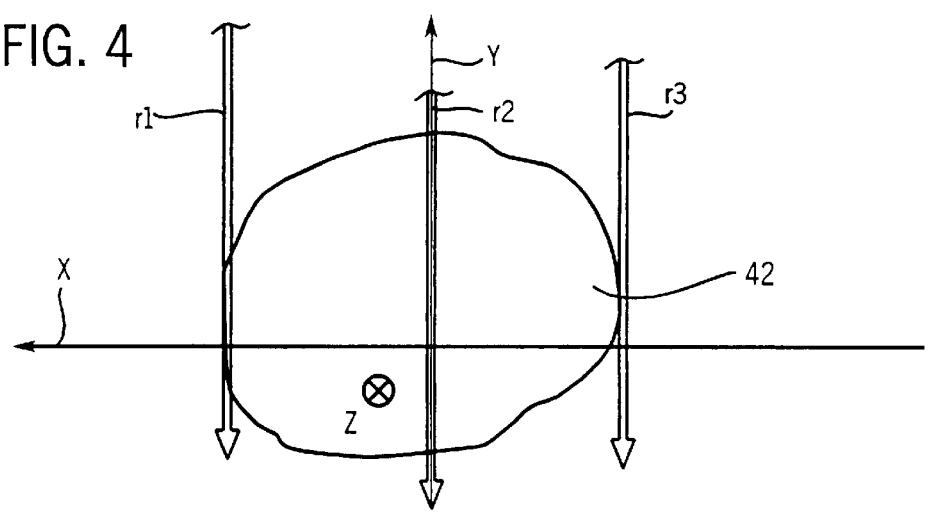
FIG. 4 is a schematic representation illustrating three fan beam rays, which pass through a patient, a separate ray corresponding to each of the fan beams of FIG. 3.

Referring to FIGS. 3 and 4, while not illustrated, each fan beam FB(β=−γ), FB(β=0) and FB(β=γ) is a multi-row beam so that data is collected for many detector array rows simultaneously. While the x-rays in each fan beam diverge from central rays (i.e. the ray along angle β in each beam), rays from different beams are parallel and therefore acquired data corresponding to parallel rays can be re-binned into parallel projections through patient 42. For example, in FIG. 3 parallel rays within beams FB(β=−γ), and FB(β=0) are identified as r1 and r2, respectively. Similarly, ray r3 in beam FB(β=γ) is also parallel to rays r1 and r2. Each of rays r1, r2 and r3 is illustrated in FIGS. 4 and 5.

Figure 5:
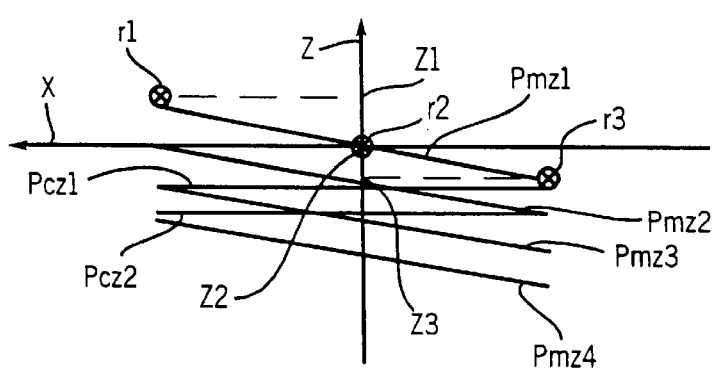
FIG. 5 is a schematic view illustrating a plurality of multi-Z parallel projections, one of the multi-Z parallel projections including each of the three rays of FIG. 4 and, also illustrating two constant-Z projections.

Referring to FIGS. 3 through 5, while parallel, rays r1 through r3 are in different positions with respect to the Z-axis and therefore, after re-binning, the resulting projections are parallel multi-Z projections. Four separate parallel multi-Z projections are illustrated in FIG. 5 and are identified as Pmz1, Pmz2, Pmz3 and Pmz4, respectively. Rays r1, r2 and r3 all correspond to projection Pmz1. In the present example it is assumed detector 44 includes four detector rows so that all of the data corresponding to projections Pmz1 through Pmz4 is collected simultaneously.

Referring still to FIG. 5, because of the multi-slice data acquisition, after the re-binning process it becomes possible to directly interpolate/extrapolate among the adjacent parallel multi-Z projections Pmz1 through Pmz4 to generate parallel constant-Z projections through patient 42. Two resulting parallel constant-Z projections are illustrated in FIG. 5 as Pcz1 and Pcz2, respectively. The interpolation/extrapolation process may be performed in any manner well known in the art including interpolation/extrapolation via linear or higher-order polynomials or other numerical methods suitable to the task (e.g., sinc( ) expansions, etc.)

After the parallel constant-Z projections Pcz1, Pcz2, etc. have been generated, reconstruction of an image in any image pane along the Z-axis proceeds as follows. First, a parallel constant-Z projection filtering process is performed. Importantly, after rebinning to parallel, each of the rays in a projection is at a same projection angle θ (i.e., the parallel projection angle) and, as the helical weights depend only upon Z, the weighting process is no longer ray-dependent. Therefore, the filtering process need only be performed once for each parallel constant-Z projection.

Referring to FIG. 2, after the parallel constant-Z projections are filtered once, the filtered parallel constant-Z projections are stored in storage system 66. Thereafter, using visual tools supported by console 65, a system operator can select any plane along the Z-axis for reconstructing an image. Once a Z-axis plane is selected, at least a subset of the filtered parallel constant-Z projections are weighted and backprojected by using any of several different backprojection algorithms as well known in the art.

The helical weight associated with a single parallel projection is a constant related to the distance between the Z-location of the projection and the Z-location of the imaging plane of reconstruction. For example, referring to FIG. 6, the distances ΔZ1 and ΔZ2 between imaging plane Pi and filtered parallel constant-Z projections Pcz1 and Pcz2 determine how projections Pcz1 and Pcz2 affect a projection in plane Pi which includes rays parallel to projections Pcz1 and Pcz2. After helical weighting and back projection a desired image results and can be viewed via console 65.

It should be appreciated that the inventive process which facilitates rapid image generation via re-binning and single filtering of multi-row CT data reduces overall processing time and hence increases system throughput. In addition, because Z-axis distances between rays in parallel constant-Z projections and the imaging plane are exact (e.g., see ΔZ1 and ΔZ2 in FIG. 6) instead of estimated, more accurate images with less artifacts result.

There are two areas in which it is believed the present invention will be extremely valuable. First, in the case of three-dimensional reconstruction typically two or more images per source rotation are generated to improve Z-resolution. This means that each data projection contributes to two or more parallel slice images and hence each projection has to be weighted and filtered two or more times during reconstruction thereby exacerbating the reconstruction process.

Second, in fluoroscopy where relative and precise positions are extremely important, some systems require many more images (e.g., 6, 12, etc.) to be generated for each source rotation which further increases the reconstruction process time required for weighting and refiltering. In both of these cases the present invention appreciably reduces reconstruction time and results in better images generally.

B. INVENTIVE PROCESS

Figure 7:
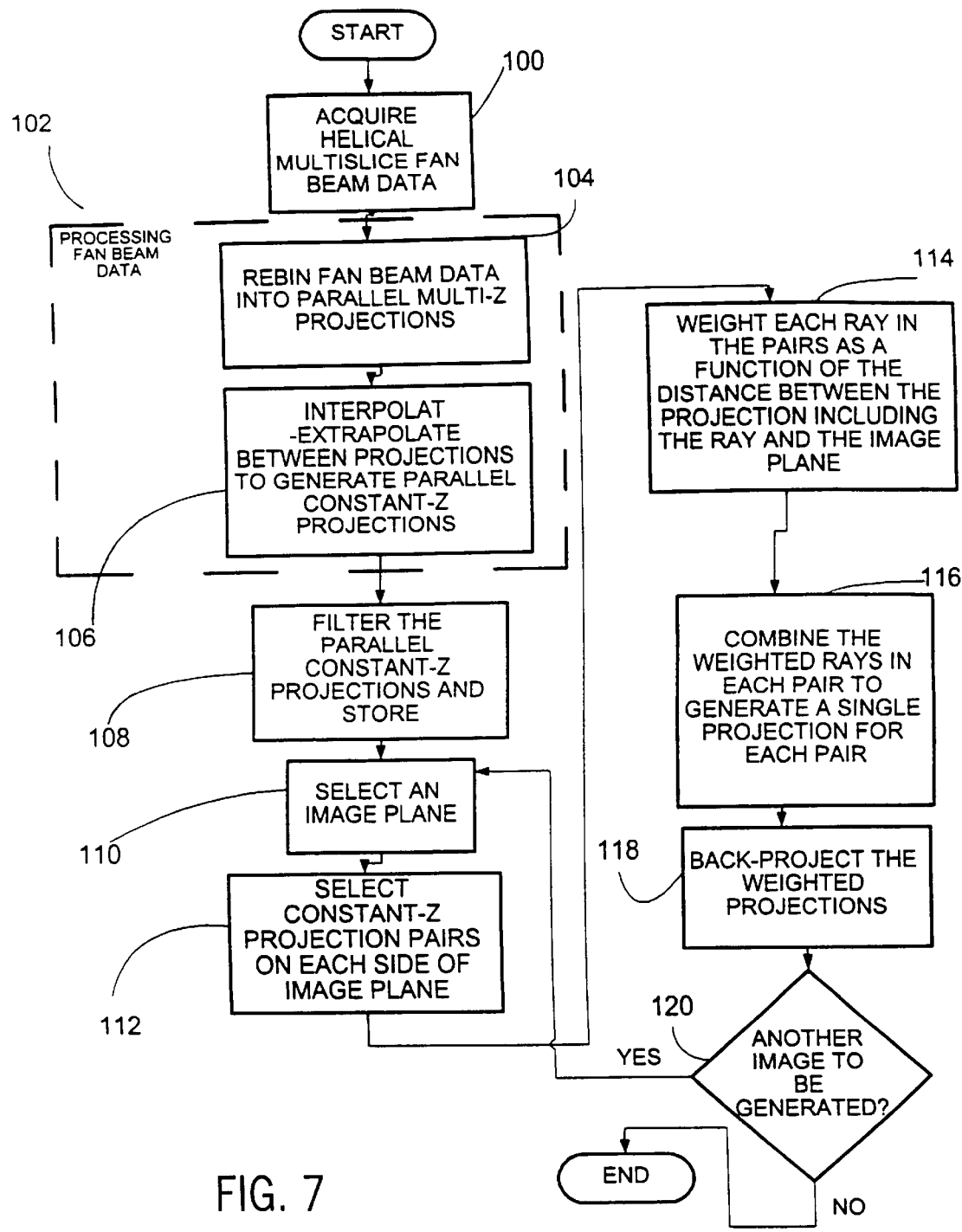
FIG. 7 is a flow chart illustrating a preferred method according to the present invention.

Referring now to FIG. 7, a flow chart representing the inventive process is illustrated. Referring also to FIGS. 1, 2 and 3, with patient 42 resting on table 43 and source 10 turned on to generate fan beam 40, table 43 is translated along axis Z (i.e., in direction indicated by arrow 48) while gantry 20 rotates so that beam 40 sweeps a helical path through a portion of patient 42 including an organ to be imaged. In FIG. 7 this data acquisition process is identified by process block 100 which results in fan beam data corresponding to beams like those illustrated in FIG. 3.

Within dashed block 102, the fan beam data is processed to generate parallel constant-Z projections. To this end, at process block 104 computer 60 rebins the fan beam data into parallel multi-Z projections. Referring also to FIG. 5, exemplary multi-Z projections are identified by numerals Pmz1, Pmz2, Pmz3 and Pmz4. Next, at process block 106, computer 60 interpolates and/or extrapolates between the parallel multi-Z projections to generate parallel constant-Z projections. Exemplary constant-Z projections Pcz1 and Pcz2 are illustrated in both FIGS. 5 and 6.

Referring still to FIGS. 2 and 7, at process block 108 computer 60 filters parallel constant-Z projections Pcz1 and Pcz2 and stores the resulting filtered parallel constant-Z projections in mass storage 66. After the filtered parallel constant-Z projections have been stored, the projections can be used to construct an image within any constant-Z imaging plane.

Figure 6:
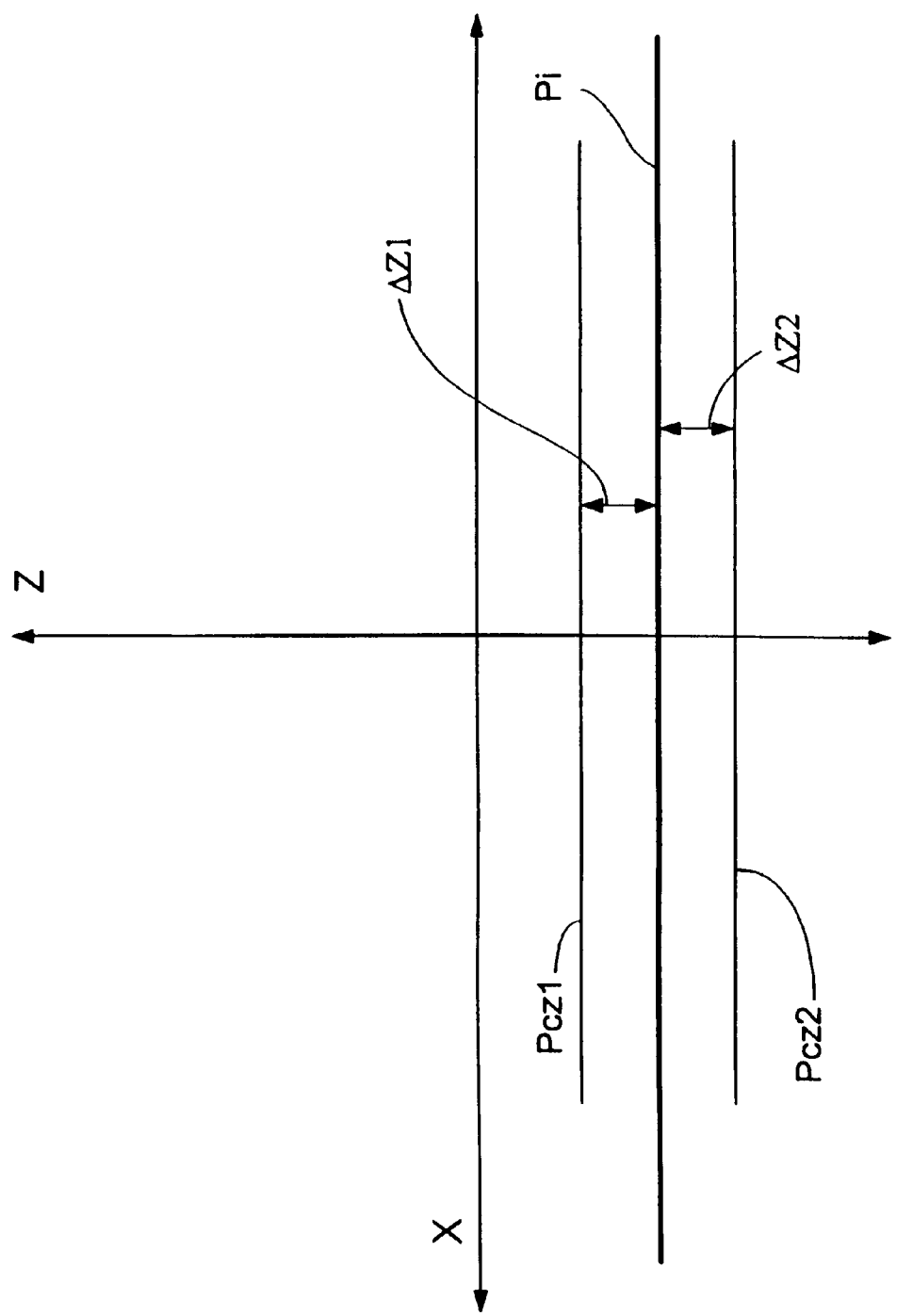
FIG. 6 is a schematic representation similar to FIG. 5, illustrating the two constant-Z projections of FIG. 5 and, also illustrating a single projection within an image plane.

To this end, referring still to FIGS. 2 and 7, at process block 110, a system operator uses console 65 to select a plane for imagery construction wherein the plane passes through the section of the patient for which fan beam data was acquired in step 100. An exemplary image plane Pi is illustrated in FIG. 6. Next, at block 112 computer 60 selects a constant-Z projection pair for each projection angle wherein each pair includes two constant-Z projections, one constant-Z projection on each side of the image plane Pi. In FIG. 6 constant-Z projections Pcz1 and Pcz2 represent an exemplary constant-Z projection pair.

At process block 114, each ray in each of projections Pcz1 and Pcz2 is weighted as a function of the distance between the projection including the ray and image plane Pi. Thus, the rays in projection Pcz1 are weighted as a function of distance ΔZ1 and the rays in projection in Pcz2 are weighted as a function of distance ΔZ2 and therefore rays in the different projections are weighted differently.

Continuing, at process block 116 the weighted rays in each pair are combined to generate a single projection for each pair. For example, referring again to FIG. 6 after weighting the rays, the rays in each of projections Pcz1 and Pcz2 are combined to form a single projection within the image plane Pi. At block 118 computer 60 back projects all of the projections which result from the combination step in block 116 to generate an image within image plane Pi. The resulting image is displayed via console 65 for the operator to view.

At decision block 120 the operator indicates, via console 65, whether or not the operator would like to generate another image. If the operator opts not to generate another image, the processor continues to display the previously generated image. If the operator selects another image control passes back to block 112 via block 110 and the process continues.

Additional advantages of the present invention result from the ability to modify two key parameters of interpolation between parallel constant-Z projections. First, interpolation width can be chosen for trade-off between z-resolution, image artifacts and image noise. During low speed data acquisition where imaging pitch is relatively low, typically the parallel multi-Z projection will include conjugate rays (i.e. rays which are adjacent along the z-axis and directed along path directions which differ by 180°) between rays corresponding to adjacent detector rows.

Figure 8:
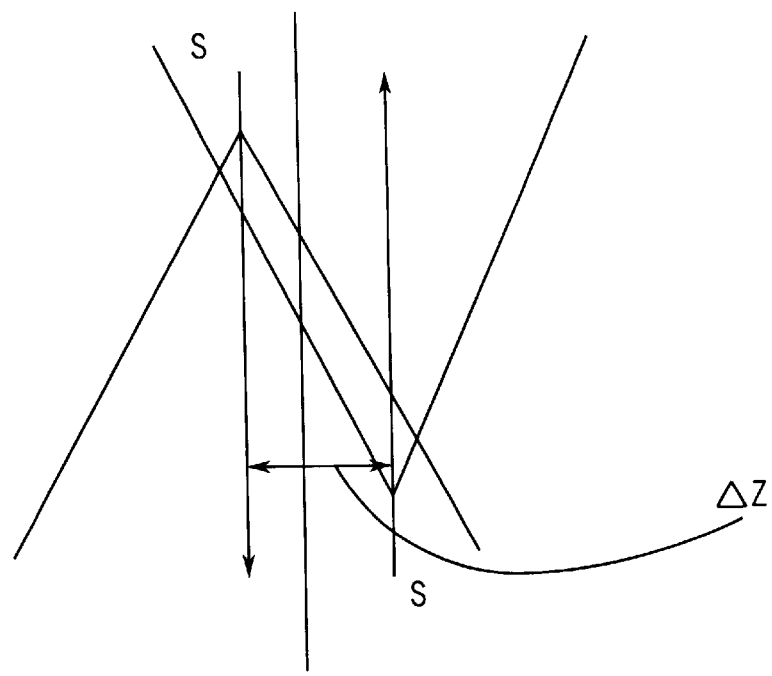
FIG. 8 is a schematic diagram illustrating conjugate rays.

In this case a narrow interpolation width hiw should be used during the interpolation step described above to generate the parallel constant-Z projections. For example, referring to FIG. 8, where $\Delta Z$ is the detector row separation on isocenter, a minimum interpolation width chosen from within a range of hiw/$\Delta Z$=0.5 and 1.0 may be chosen, the selection from within the range 0.5 and 1.0 affecting the noise, Z-resolution and image artifacts in different manners.

Figure 9:
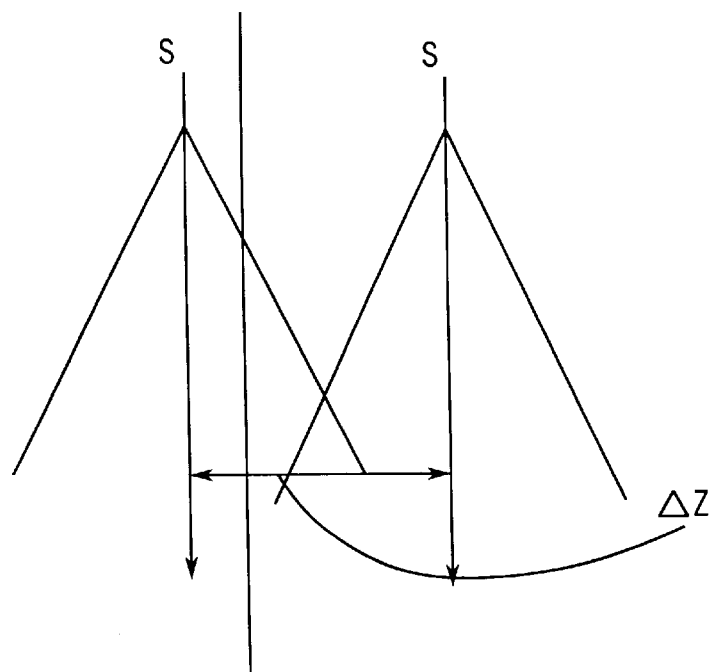
FIG. 9 is a schematic similar to FIG. 8, albeit illustrating rows from adjacent rays.

On the other hand, for high speed data acquisition modes and in particular where no conjugate ray is available to high pitch, to avoid streak type artifacts it is necessary to use a "wide" interpolation width. For example, referring to FIG. 9 where $\Delta Z$ is again the detector row separation on isocenter, a relatively wide interpolation width hiw/$\Delta Z$ of 2.0 may be used. Backprojection of only 180° worth of parallel projections may be used to generate an image.

Second, in addition to modifying the interpolation width hiw to achieve imaging advantages, additional advantages may be achieved by changing the interpolation function to vary the reconstructed image thickness.

One model for changing the interpolation function is to employ a Z-smoothing technique such as the one described in the article entitled "Helical CT Reconstruction with Longitudinal Filtration" by H. Hu and Y. Shen which was published in Med. Phys. 25(11), November 1998. Thus, by including data from constant-Z projections which are relatively further away from desired imaging plane in data which affect the resulting image the effective image thickness is modifiable. Once again, the helical weight associated with a given projection is a constant for all rays within the projection and depends only on the distance between the Z-coordinate of the projection and the Z-coordinate of the reconstruction image plane.

It should be understood that the methods and apparatuses described above are only exemplary and do not limit the scope of the invention, and that various modifications could be made by those skilled in the art that would fall under the scope of the invention. For example, while the techniques and methods described above are described in the context of a relatively low speed data acquisition system, clearly the techniques and methods could be used with high speed data acquisition systems where data required for generating an image within an image plane is acquired during less than a full source rotation. In addition, in this case, the rebinning to constant-Z projections could be performed to rebin to a specific image plane so that interpolation in not subsequently required.

To apprise the public of the scope of this invention, I make the following claims:

I claim:

1. A method for use with a computerized tomography (CT) system including a fan beam source and a multi-row detector arranged on opposite sides of a Z-axis, the source and detector rotated about the Z-axis as a patient traverses there along to generate helical imaging data, the method for generating at least one image within an imaging plane from the helical data and comprising the steps of, after acquiring fan beam helical imaging data:

processing the fan beam helical data to generate parallel constant-Z projections proximate the imaging plane;

filtering the parallel constant-Z projections; and mathematically combining the parallel constant-Z projections as a function of the spatial relationships between the imaging plane and the constant-Z projections to generate the at least one image;

wherein the step of mathematically combining the parallel constant-Z projections includes weighting a sub-set of the constant-Z projections, combining the subset of weighted projections to generate a set of image projections and back-projecting the image projections to generate the image.

2. The method of claim 1 wherein the step of weighting a subset includes selecting constant-Z projection pairs, each pair including a first constant-Z projection on a first side of and adjacent the imaging plane and a second constant-Z projection on a second side of and adjacent the imaging plane and weighting each projection pair ray as a function of the distance in Z between the projection including the ray and the image plane and wherein the step of combining the subsets includes, after the projection rays have been weighted, combining the rays in each projection pair into a single projection to be back-projected.

3. The method of claim 1 also for generating a second image within a second imaging plane from the helical data and comprising the steps of, after filtering, selecting constant-Z projection pairs, each pair including a first constant-Z projection on a first side of and adjacent the second imaging plane and a second constant-Z projection on a second side of and adjacent the second imaging plane and weighting each projection pair ray as a function of the distance in Z between the projection including the ray and the second image plane, combining the subset of weighted projections to generate a set of image projections and back-projecting the image projections to generate the image.

4. The method of claim 3 wherein the step of combining the subsets includes, after the projection rays have been weighted, combining the rays in each projection pair into a single projection to be back-projected.

5. An apparatus for use with a computerized tomography (CT) system including a fan beam source and a multi-row detector arranged on opposite sides of a Z-axis, the source and detector rotated about the Z-axis as a patient traverses there along to generate helical imaging data, the apparatus for generating at least one image within an imaging plane from the helical data and comprising:

a processor running a pulse sequencing program to perform the steps of:

processing the fan beam helical data to generate parallel constant-Z projections proximate the imaging plane;

filtering the parallel constant-Z projections; and mathematically combining the parallel constant-Z projections as a function of the spatial relationships between the imaging plane and the constant-Z projections to generate the at least one image;

wherein the processor runs the program to perform the step of mathematically combining the parallel constant-Z projections by weighting a sub-set of the constant-Z projections, combining the subset of weighted projections to generate a set of image projections and back-projecting the image projections to generate the image.

6. The apparatus of claim 5 wherein the processor runs the program to perform the step of weighting a sub-set by selecting constant-Z projection pairs, each pair including a first constant-Z projection on a first side of and adjacent the imaging plane and a second constant-Z projection on a second side of and adjacent the imaging plane and weighting each projection pair ray as a function of the distance in Z between the projection including the ray and the image plane and wherein the processor runs the program to perform the step of combining the subsets by, after the projection rays have been weighted, combining the rays in each projection pair into a single projection to be back-projected.

7. The apparatus of claim 5 also for generating a second image within a second imaging plane from the helical data, to this end, the processor running the program to perform the steps of, after filtering, selecting constant-Z projection pairs, each pair including a first constant-Z projection on a first side of and adjacent the second imaging plane and a second constant-Z projection on a second side of and adjacent the second imaging plane and weighting each projection pair ray as a function of the distance in Z between the projection including the ray and the second image plane, combining the subset of weighted projections to generate a set of image projections and back-projecting the image projections to generate the image.

8. The apparatus of claim 7 wherein the processor runs the program to perform the step of combining the subsets by, after the projection rays have been weighted, combining the rays in each projection pair into a single projection to be back-projected.

\* \* \* \* \*